(12) United States Patent
Deur

(10) Patent No.: US 11,534,590 B2
(45) Date of Patent: Dec. 27, 2022

(54) CONTROLLED ARTERIAL/VENOUS ACCESS

(71) Applicant: Tomislav Deur, Hollidaysburg, PA (US)

(72) Inventor: Tomislav Deur, Hollidaysburg, PA (US)

( * ) Notice: Subject to any disclaimer, the term of this patent is extended or adjusted under 35 U.S.C. 154(b) by 828 days.

(21) Appl. No.: 16/288,084

(22) Filed: Feb. 27, 2019

(65) Prior Publication Data
US 2020/0269030 A1    Aug. 27, 2020

(51) Int. Cl.
  *A61M 39/02*    (2006.01)
  *A61M 25/06*    (2006.01)
  *A61M 1/36*     (2006.01)

(52) U.S. Cl.
  CPC ...... *A61M 39/0208* (2013.01); *A61M 1/3653* (2013.01); *A61M 25/065* (2013.01); *A61M 39/0247* (2013.01); *A61M 2039/0223* (2013.01)

(58) Field of Classification Search
  CPC .............. A61M 39/28; A61M 39/0208; A61M 2039/0223; A61M 1/3653; A61M 39/284; A61M 2039/0202; A61M 2039/0258; A61M 39/0247; A61M 25/065; A61M 1/3655; A61M 1/3661; A61M 1/3659; A61B 17/11; A61B 2017/1107; A61B 2017/12004
  See application file for complete search history.

(56) References Cited

U.S. PATENT DOCUMENTS

| 4,015,601 | A  | * | 4/1977 | Bokros    | A61M 39/0247 604/175 |
| 4,092,983 | A  | * | 6/1978 | Slivenko  | A61M 39/0247 604/175 |
| 4,804,369 | A  | * | 2/1989 | Lapeyre   | A61M 39/0247 604/891.1 |
| 4,822,341 | A  | * | 4/1989 | Colone    | A61M 1/3655 604/249 |
| 6,544,214 | B1 | * | 4/2003 | Utterberg | A61M 39/0208 604/93.01 |
| 2014/0276327 | A1 | * | 9/2014 | Deur | A61M 39/28 604/6.16 |

* cited by examiner

*Primary Examiner* — Theodore J Stigell
(74) *Attorney, Agent, or Firm* — Ramberg IP, LLC; Jeffrey R. Ramberg

(57) ABSTRACT

Apparatus and methods for controlled arterial/venous access are provided. The apparatus and methods may include a lumen anastomosed to a bodily lumen. A lumen clamping means may utilize a clamp manipulator to effectively seal the tubing, and the manipulator may be operated by two fingers. A needle receptor may be utilized, and the receptor may utilize a compressible member to seal tightly against a needle inserted from outside the body, in order ensure secure placement into a channel. The channel may be in liquid communication with the tubing. The manipulator and the needle receptor may be palpable from outside the body.

19 Claims, 7 Drawing Sheets

CONTROLLED ARTERIAL/VENOUS ACCESS

FIELD OF TECHNOLOGY

Aspects of the invention relate to a controlled port for accessing a blood vessel.

BACKGROUND

Various therapeutic treatments require access to blood flowing through a circulatory system. For example, treatments in the fields of hematology, oncology and/or pharmacology may require direct access to circulating blood. Some treatments, such as dialysis, require an extraction and reintroduction of blood. The blood extracted from the body is filtered, waste products are removed and the filtered and "clean" blood is reintroduced into the circulatory system.

To perform dialysis, it is necessary to have access to the blood, while it is in circulation. Additionally, the access to the blood should be arranged to provide a high extraction throughput or flow rate. The flow rate allows a sufficient amount of blood to be extracted within a given period of time. Efficacy of the dialysis procedure may be dependent upon the extraction throughput. Treatment costs as well as patient comfort usually coincide with efficient procedures.

When performing dialysis, one method of accessing the blood is via an intravenous catheter. The catheter may be inserted into a large vein. Large veins, such as the vena cava, jugular vein or femoral vein, allow for a higher extraction throughput than do other veins.

However, a catheter is a foreign body in the vein, and may trigger venous stenosis in or around the vein wall. The venous stenosis may scar and occlude the vein. As a result of the stenosis and occlusion, multiple access sites must be utilized and a patient on long term dialysis may "run out" of usable veins for catheter access. In addition, a catheter protrudes out of a patient's skin, and staving off infection is a common challenge when employing catheter access. However, the patient may desire catheter access because, after insertion, accessing the patient's blood through connection of the catheter to a dialysis machine does not require repeated needle pricks.

Another access method is to surgically form an arteriovenous ("AV") fistula. To form the fistula, a surgeon joins an artery to a vein, bypassing narrow capillaries. Arteries carry blood away from the heart and blood typically flows faster, and at a higher pressure, through arteries than veins. By transferring directly from an artery to a vein without intervening capillaries, blood flows swiftly at a high pressure from the artery into the vein. A fistula is formed by creating an anastomosis between and artery and vein. However, the fistula may take 1-4 months to mature the vein prior to being accessed for dialysis.

After maturity, two needles are inserted into the vein distal to the fistula anastomosis. A first needle extracts blood which is transferred to a dialysis machine. A second needle receives the filtered blood from the dialysis machine and reintroduces the filtered blood into the vein.

A fistula is characterized by lower infection rates than catheter access. However, because the fistula is always "on" and blood is always flowing through the fistula, the fistula may stimulate a "steal syndrome." The steal syndrome occurs when insufficient blood flow reaches the bypassed capillaries. Blood may be drawn through the fistula and returned to general circulation through the vein, preventing adequate blood flow to extremities of a limb. The steal syndrome may result in coldness in the extremities and ischemic tissue damage if severe. Since the fistula is always "on", some patients face issues with cardiac failure since their heart is now tasked with a constantly increased cardiac output. If the patient's heart is unable to perform at such a cardiac output, it can lead to congestive heart failure.

A fistula may also be associated with development of an aneurysm in the vein. While undergoing dialysis, needles must be regularly inserted into veins distal to the fistula to reintroduce blood to the circulatory system. The needle insertions may weaken a wall of the vein, as they must be repeated for every treatment. The repeated needle sticks may be repeated at convenient, or easily accessible, areas in the anatomy, thereby increasing the likelihood of an aneurysm.

Another dialysis access method is to create an AV graft. The graft operates under principles similar to the fistula. The graft is an artificial conduit that transfers blood flow from an artery directly into a vein. Unlike the fistula, the graft joins the artery and vein using a synthetic material. Unlike a fistula, a graft does not need to mature allowing for earlier usage, and may be used in cases where a patient's anatomy is not optimal for creation of a fistula. The graft may be made of a length sufficient to join two blood vessels distant from each other.

However, grafts are made from synthetic materials, and are foreign to the body. While a synthetic graft may be sized ideally to the anatomy, they are associated with a higher rate of thrombosis. The thrombosis may result from stenosis within natural arteries and veins adjacent to the anastomoses at each end of the graft. Grafts are also typically associated with a higher rate of infection than the fistula. Furthermore, like a fistula, a graft cannot be turned "off," and even after completion of a dialysis procedure, blood is constantly flowing through the graft. Again, this situation is not ideal for the tissue which may be transfusing significantly less blood than normal.

It would be desirable to obtain benefits of a fistula/graft without these numerous associated disadvantages. It would be desirable to provide blood access that is associated with a high throughput and that may be "turned off" after a treatment. It would be desirable to provide regular access to blood without damaging a blood vessel as a result of repeated needle pricks. Therefore, it would be very beneficial to provide apparatus and methods for a valve for accessing a blood vessel.

SUMMARY OF THE INVENTION

A vascular access device is described herein, along with methods for use, wherein repeated access to a bodily lumen may be predictably obtained. The device may be implanted in order to gain access to a lumen in the body of a being without the need for an organic or synthetic graft to be utilized; the instant device may directly access an artery or a vein. Using two devices, a first may access an artery, while the second accesses a vein. Alternatively, two devices may be used to access the venous system. These examples are not meant to be limiting, but rather, they are to serve as illustrative examples of how and where the instant device may be employed. Those skilled in the art can imagine various placements that could be made with a device that can access a bodily lumen, especially when a traditional graft does not need to be placed, or when a graft can not be placed for medical or anatomical reasons. Instances using two devices can provide access points that are not necessarily close in proximity with each other, this would allow the best anatomical location to be selected for access.

Devices such as those described herein may be used for a wide variety of medical procedures, treatments, and diagnostics. By way of example, a pair of devices disclosed herein could be utilized in a dialysis setting, additionally a single device could be used for infusion of drugs or other treatment fluids and compounds, or similarly the extraction of bodily fluids may be conducted through a single device. While two devices may be utilized in a preferred embodiment, one device from the pair may be selectively used to quickly gain access to a lumen, in order to perform a procedure other than what may have originally been intended.

A preferred arrangement for this subcutaneous vascular access device, that would allow repeated access to a predetermined native body vessel would include a lumen and a housing. The lumen would extend from the housing, located at a lumen proximal end and an anastomosis junction with a blood vessel, at the lumen distal end. The lumen would be in fluid communication with the native body vessel and the housing. The fluid flow through the lumen would be selectively sealed by a clamp. The clamp would be located on the proximal side of the anastomosis junction, and it would be placed such that it would not interfere with blood flow through the native body lumen.

In this preferred embodiment, the housing contains at least one funnel shaped needle receptor, a spherical hollow chamber, and at least one clamp actuator that is mechanically linked to the clamp and is arranged to selectively actuate the clamp.

In a preferred embodiment the funnel shaped needle receptor is selectively in fluid communication with the hollow spherical chamber and the needle receptor is arranged coaxially on an axis that intersects the hollow spherical chamber at a point that is tangential to the outer surface of the hollow spherical chamber, such that the hollow spherical chamber is in fluid communication with the lumen. The funnel shaped needle receptor is basically a truncated cone in its simplest form, but other geometries are envisioned to be within the scope of the present disclosure; a key feature of the is element is that the needle is guided to the proper location, such that a proper seal may be obtained and safely maintained during a dialysis or other procedure. Similarly, the spherical chamber need not be perfectly round in all orientations; it is envisioned that a minor deviation at the point of fluid entry or fluid exit may serve to allow even flow through the chamber and the lumen. The goal is to avoid stagnate areas, or areas with uneven flow volume or flow rate, such that clotting is avoided during a procedure in which blood is flowing within the device. This spherical geometry with tangential inlet and outlet access pathways has shown to be very effective in avoiding these types of fluidic disturbances.

The clamp may be actuated with a device that depresses like a tab on the side of the housing, and there may be tab-like actuators on both sides of the housing. These tabs may be palpable from outside the body. The tab or tab arrangement may be manually depressed, which causes a force to be transmitted through a mechanical linkage to the clamp; the linkage would be arranged to cause the clamp to open and thereby allow fluid flow through the lumen.

In a preferred embodiment, the lumen has mechanical integrity but does not necessarily need to be rigid. Its composition is preferably polymeric in nature, for the ease of manufacture. However, it may be monolithic, or it could be a composite, or a complex aggregate of materials. A preferred embodiment is a kink-resistant polymer tube substrate with a stiffened polymeric or metallic coil laminated or otherwise affixed to the tube.

Various of the components in the instant device would likely be made from polymers, however many advances in metallic materials allow flexibility and favorable elastic properties; furthermore, metals and polymers have been fabricated with shape memory properties. Certain components of the instant device might benefit from these alternative materials and their properties. Many of these materials are biocompatible, and suitable for implant, and coating technology has rendered alloys not typically favorable for implantation to be considered. The scope of this disclosure is meant to include these alternate materials, and these are familiar to those skilled in the art; and the lack of repetition of these options is not meant to be limiting, but rather omissions for the sake of brevity.

In a preferred embodiment the device is of a fixed length, but it is contemplated that various lengths may be made available such that various types of anatomy may be accommodated. Especially in longer lumen lengths, the materials of manufacture may be somewhat flexible, while maintaining good compressive strength and kink resistance.

In yet another preferred embodiment, the funnel shaped needle receptor houses an elastomeric sealing material having an opening which permits passage of the hollow needle. In this embodiment, as well as exemplary embodiments detailed elsewhere in this specification, the funnel shape serves to align the needle with the region housing the sealing material. This region may be at the center of said funnel, but designs with an offset needle approach path may be beneficial.

In yet another preferred embodiment, the actuating force is transmitted through a mechanical linkage to said funnel shaped needle receptor, and applies pressure to said elastomeric sealing material which is arranged to deform and tightly conform around an outer surface of said hollow needle, thereby forming an impenetrable seal against the outer surface of the needle. The linkage construct may be in the form of flat rods, connected with pins which allow movement in a rotational and linear fashion. The linkage may be of any cross-section, and the linkages may be of an arcuate shape in order to provide a stiffening effect to the linkage. There may be a plurality of components arranged as components to the linkage, allowing complex movement in the "x" and "y" directions. Some linkage members may contain slots or keyways arranged to allow non-uniform displacement resulting in a mechanical advantage being gained by certain selected linking members. This non-uniform displacement can be used to drive components to varying degrees, or the mechanical advantage may be utilized to drive components that have more resistance.

The clamp actuator mechanism may further comprises a lock-out button having an first position and a second position, wherein the lock-out button may be located on the top of the housing and it may also be palpable from outside the body. The lock-out button, while in its first position, prevents opening of the clamp, and the lock-out button is in its second position, it allows the mechanical linkage to move which in turn causes the opening of the clamp.

In yet another preferred embodiment, the needle, upon insertion through the opening in the elastomeric sealing material causes the displacement of a sealing rod which was slidably arranged in the opening, whereupon the displacement of the rod causes energy to be stored in a spring or other elastic member, such that upon removal of said needle, said sealing rod reverses its travel through said opening, thereby sealing said opening. Thus, there is no (or minimal)

leakage from the proximal end of the device; when the device is not being used, the sealing rod is sufficient to block any flow of fluid from the lumen (vis-à-vis the spherical chamber pathway). The elastomeric member need not seal against the sealing rod with great force, since the clamp will be closed during periods of non-use and pressure in the fluid in the lumen should be minimal. In the instance of accidental withdrawal of the needle prior to completion of the procedural cycle, the clamp may remain open as the safety button has not been pushed a second time. This may lead to some leakage at the proximal end of the device, however the sealing rod provides an effective physical barrier to flow; therefore leakage, if any, can be expected to be minor.

In yet another embodiment the clamp actuator may be linked to the clamp by a mechanical linkage that includes various arrangements of flat rods, a pull cable, a push rod, or a lever arrangement, such that movement of said tab results in an indirectly proportional movement of the clamp. Likewise, the same mechanical linkage may be used, or a similar linkage, to cause an indirectly proportional movement of the funnel shaped needle receptor. The degrees or amounts of movement are indirectly proportional, because each element needs to move a distinct amount, and these amounts are not the same. Additionally, a mechanical advantage may be gained by such a linkage where a lever or fulcrum type of assembly is employed. For example, in a preferred embodiment the clamp linkage may cause movement of 2 to 10 millimeters while the same linkage could be designed to move the needle receptor only 1 to 5; each of these amounts can be obtained with a tab movement of 1 to 3 millimeters. Generally, preferred embodiments utilize movement of said funnel shaped needle receptor are less than 50% of the movement of the clamp; for example, a prototype has been developed that initiates with 2.5 mm of tab movement and utilizes a linkage to generate 6 mm of pulling cable movement to operate a clamp, while the same linkage generates a reduction of displacement to cause a 0.5 mm movement of the needle receptor.

Another preferred embodiment of the present invention utilizes a subcutaneous vascular access device designed to selectively provide fluid communication between a needle inserted from outside the body and a native bodily vessel within a body. The device is constructed from a lumen and a housing, with the lumen extending between said housing located at a lumen proximal end and an anastomosis junction with a blood vessel. The anastomosis junction is located at a lumen distal end, wherein said lumen is in fluid communication with the native body vessel and said housing, wherein fluid flow through the lumen is selectively sealed by a clamp. The clamp is located adjacent and proximal to said anastomosis junction. The anastomosis junction is further arranged to accept a standard anastomosis known to those skilled in the art, wherein the anastomosis affixes the lumen to a native bodily vessel.

In this preferred embodiment the housing may comprise at least one funnel shaped needle receptor, a spherical hollow chamber, a safety button, and at least one clamp actuator that is mechanically linked to said clamp through a lever system whereby said clamp actuator is arranged to selectively actuate said clamp. In this instance, the funnel shaped needle receptor is selectively in fluid communication with said hollow spherical chamber and said funnel shaped needle receptor is arranged coaxially with an axis that intersects said hollow spherical chamber at a point that is tangential to said hollow spherical chamber, and further, wherein said lumen is in fluid communication with said hollow spherical chamber.

The clamp actuator of this and various other embodiments, further comprises at least one tab, wherein the tab is connected to said lever system in a rotationally sliding arrangement. This design allows transverse movement inside the housing, while allowing the concomitant rotational component of such movement. This type of design also allows for the gaining of mechanical advantage of a step-down of linear movement, as necessary.

A safety switch is generally used, and it is usually in the form of a button which is arranged to be operable in positions that include a locked state and an unlocked state, wherein said locked state prevents movement of the tab, or tabs if more than one is used. Pressing the safety button toggles it to an unlocked state where the tab may be depressed. In this preferred embodiment, depressing the tab causes the lever system to displace said funnel shaped needle receptor and a cable member.

The funnel shaped needle receptor, in a preferred embodiment, further comprises an elastomeric sealing material having an opening therein arranged to permit insertion of said needle therethrough. The insertion of the needle results in the needle being in fluid communication with the lumen through a contiguous pathway that includes flow through said hollow spherical chamber.

The said funnel shaped needle receptor, of a preferred embodiment, is arranged to compress the elastomeric sealing material between the needle receptor and said housing in response to the movement of the tab or tabs. Embodiments may function with one tab, however it has been shown the having a tab on opposing sides of the housing creates a favorable orientation from an ergonomic as well as mechanical standpoint.

The cable member is preferably slidably arranged between the clamp actuator and the clamp, wherein displacement from movement of the tabs causes said cable member to translate force from said clamp actuator to said clamp, where said force serves to cause said clamp to be manipulated from a closed position to an open position, with said open position being arranged to allow fluid communication between said lumen and said native bodily lumen. The needle insertion provides fluid communication with the lumen, vis-à-vis the hollow spherical member, and the clamp actuator establishes fluid communication from the lumen to the native body lumen, vis-à-vis the open clamp. Thus, the action of needle insertion together with tab depression renders the needle (from outside the body) in fluid communication with a native bodily artery.

In yet another preferred embodiment, the housing further comprises a springback mechanism arranged to absorb energy during the displacement of said cable member (resulting from the pressing of the tabs). The springback mechanism may be a simple metallic spring, or it may be an elastomeric material made from polymers, or a combination thereof; this member is designed to elastically absorb energy to provide an energy or force to drive the mechanism in the opposite direction. Many materials known to those skilled in the art, are capable of performing this function, and various design constructs utilizing those materials are contemplated by this disclosure. In a preferred embodiment, the reversing energy will be released upon the pressing of the safety button when said safety button is in the unlocked state.

The release of the springback energy forces the tab back to its original position, thereby releasing the force on said cable member such that said cable member returns to its original position. This causes the clamp to close, thereby clamping the lumen and discontinuing the fluid communication between the lumen and the native bodily lumen.

In a preferred embodiment the safety button further comprises a latch, with said latch serving to receive and releasably lock a portion of the lever system when a predetermined amount of displacement of the cable member is achieved.

The reversing or springback energy further serves to move the funnel shaped needle receptor back to its original position, wherein the compressive force on the elastomeric sealing material is released, which in turn causes an elastic recoil energy in said piston to push said needle out of said funnel shaped needle receptor, thereby ceasing fluid communication between said needle and said lumen. Additionally, the return of the funnel shaped needle receptor to its original position seals said lumen proximal end and the closing of the clamp seals the lumen distal end, thereby creating a volume of fluid stored in said device during non-use.

In yet another preferred embodiment, the housing further includes a second funnel shaped needle receptor, arranged coaxially with an axis that intersects said hollow spherical chamber at a point that is tangential to said hollow spherical chamber, and this second needle receptor allows needle insertions to be made at multiple locations on the skin surface. This is useful as the device becomes used repeatedly over time, since the skin may deteriorate or become sensitized to the cumulative injury from the needle punctures. This also provides an alternate in the event that a sealing member becomes damaged or worn from repeated use.

Similarly, in a preferred embodiment, the housing contains a second tab. The second tab, in designs containing a second tab, forms a part of the clamp actuator, with said second tab being further arranged to be connected to said lever system in a rotationally sliding arrangement, or in an arrangement similar to that of the first tab.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE DISCLOSURE

Figure 1:
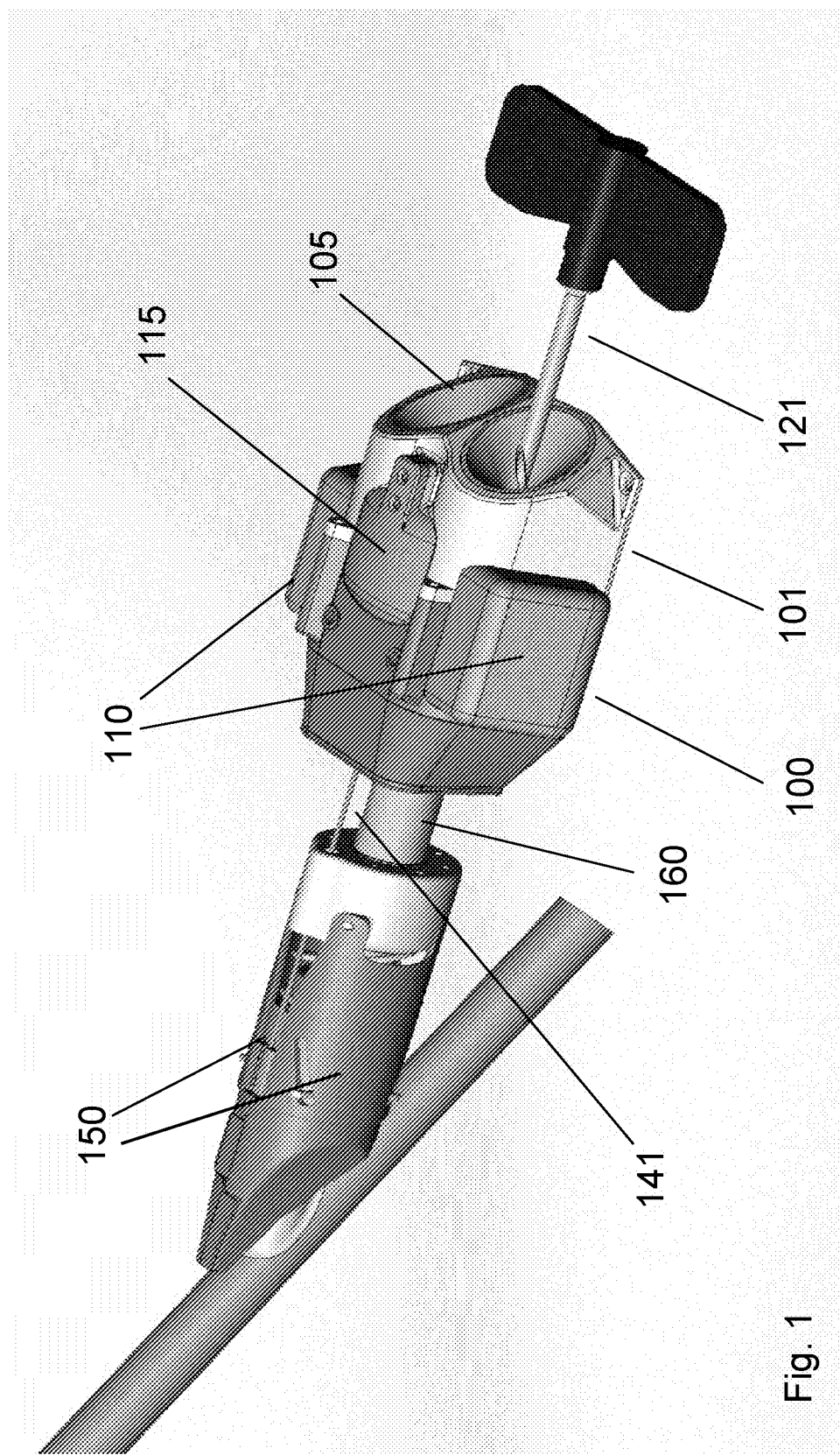
FIG. 1 shows an illustrative apparatus in accordance with principles of the invention.

Apparatus and methods for an access valve having mechanical linkages are provided. In another embodiment, an apparatus and method for an implantable subcutaneous access valve having palpable elements are provided.

Apparatus may include, and methods may involve, a transport system. The transport system may include a port. The port may be coupled to a blood vessel. The blood vessel may be an artery. The blood vessel may be a vein. The blood vessel may be any suitable blood vessel. The access valve may be coupled to any suitable conduit carrying a medium.

The port may include a spherical chamber. The port may include a mechanical linkage arrangement to transmit forces to actuate clamp means and sealing means. The port may include a sealable passageway. The port may include an orifice. The orifice may allow blood to flow between the blood vessel and the port.

The transport system may include a locking mechanism. The locking mechanism may prevent premature movement of components of the device. The locking mechanism in a second state may prevent the release of components until the locking mechanism is actuated.

Apparatus may include, and methods may involve, a graft. The graft may be attached to a conduit. The conduit may be an artery or a vein or a carrier or any suitable medium. The graft may include tubing configured to be anastomized to the conduit. The tubing may include a compressible portion. The tubing may include a non-compressible portion.

Methods may include accessing a blood vessel via a graft anastomized to the blood vessel. The method may include inserting a needle through a needle access device The methods may include directing blood, via the lumen, from the blood vessel to a spherical chamber, in fluid communication with an inserted needle. Methods may include extracting the blood from the spherical chamber. The blood may be extracted using the needle inserted through the needle access into the spherical chamber, or adjacent to, but in fluid communication with the spherical chamber.

The graft may be a first graft. The methods may include transferring blood extracted from the access valve to a dialysis machine and filtering the blood. The filtered blood may then be transferred to a second access valve. The methods may include reintroducing the filtered blood to circulation via a second graft.

The first graft may be anastomized to an artery. The first graft may be anastomized to a vein. The second graft may be anastomized to a vein. The second graft may be anastomized to an artery. In some embodiments, a plurality of grafts may be implanted. Each of the plurality of grafts may be anastomized to one or more blood vessels.

In an embodiment of a subcutaneous vascular access device, there are basically three preferred elements a needle receptor, a device lumen, and lumen clamping means. The needle receptor is subcutaneously located while portions of the clamping means lies deeper; the device lumen is the physical connection between the subcutaneous portions of the device and the deeper portion of the device, it also provides fluid communication between the needle receptor and a native body lumen. Similarly, the portions of the lumen clamping means that are meant to be actuated by hand (preferably with two fingers) are subcutaneous, while the portion contacting the device lumen are arranged to be deeper, such that the orientation provides an effective seal without creating any clotting or turbulent flow potential. This improved sealing method is targeted to reduce neo-intimal hyperplasia and stenosis formation commonly associated with aberrant vascular geometry caused by non-uniform device lumens or device protrusions which cause turbulent blood flow. Many anastomotic devices do not create a uniform surface at the area they serve to seal, thus creating pockets of stagnant blood, or eddies in the blood flow path or contiguous with the blood stream.

The needle receptor will optimally be palpable and located just beneath the skin surface. At the distal tapering aspect of each needle receptor is basically funnel shaped geometry, and In one embodiment, there will be a ball-valve mechanism, where the act of physically inserting the dialysis needle into, and through, the funnel will supply the required force to open the ball-valve mechanism and simultaneously allow the dialysis needle to pass through the funnel and into the blood lumen. In another embodiment, the needle receptor provides a funnel shaped geometry, having an elastic sealing material at or near narrowed end of the funnel. The elastic sealing material is configured to serve as a sealing ring. The sealing material is provided with an opening through which a displaceable sealing rod would be inserted to block unwanted flow through the opening. Upon insertion of the needle through the funnel shaped needle receptor, and through the opening of the sealing material, the advancing needle displaces the sealing rod, for example, either compressing the rod axially, or urging the rod against a compressible material, such where the sealing rod is supported by a spring, or spring loaded member, and upon the rod being displaced by the needle, as it is advanced, compresses the spring or collapsible rod. With the needle in place within the needle receptor, the clamp on the lumen may be opened to allow fluid flow through the lumen, and dialysis (or other procedure) may be performed so long as the needle remains in place. Upon the needle being removed from the funnel shaped element of the needle receptor, the sealing rod will be urged, such as by the compressed spring, and again be directed through the opening in the sealing material vacated by the withdrawn needle. In this manner, as the needle is removed from the funnel, the sealing rod fills the opening and fluid flow will be blocked from entering or exiting through the funnel. Thus, in the event of needle removal, prior to the clamp on the lumen being shut, the sealing rod will be urged back to the initial position and fill the opening left by the needle in the sealing material. The rod thus serves as safety seal to prevent undesirable free flow of fluid out from the lumen in the event of premature needle withdrawal.

For the various embodiments described herein, optimally, there will be multiple locations for directing a needle into the needle receptor, at distinct positions. For example, providing two needle entry points, may allow the access to be sequenced through each, in order to promote skin healing between being accessed.

In an embodiment, the chamber will optimally have an almost spherical cross section configuration so that blood cannot settle into any corner.

For the various embodiments described herein, the clamp is optimally located where the anastomosis between the device lumen and native vessel is located. The clamp runs substantially parallel to the long axis of the native vessel in the form of two rod-like members that flank the distal most aspect of the device lumen, optimally at a position immediately above the anastomosis with the native vessel (for the sake of this description, the distal end of the device lumen and the anastomosis site may be considered one and the same when discussing the clamping location form and function). The rods will be connected to one another, at one end, such that in the closed position, they compress the distal end of the device lumen preventing blood from entering and stagnating in the device lumen. The clamp is further designed to minimize the blood exposure to the device's blood lumen to optimize for nearly laminar blood flow in the native lumen when the clamp is closed and the device is not in use. When the clamp is opened, blood will enter the device lumen through the anastomosis. The clamp is opened using the force generated by the fluid driven member of the device, or alternatively by mechanical linkages transmitting forces applied to palpable elements placed subcutaneously, as will be discussed.

In an embodiment relying on mechanical linkages for transmitting forces, there are provided on the device implanted subcutaneously, one or more tabs that are palpable through the skin, and configured to be manipulated by the user by applying pressure to the one or more tabs. The movement of the one or more tabs, are configured to actuate via mechanical linkages, preferably levers, the clamp to open the lumen for fluid flow therethrough. Additionally, the mechanical linkages are configured to cause movement of at least a portion of the needle receptor, thereby applying a compressive force to the elastic sealing material, whereupon the sealing material will be squeezed tightly against the outside surface of the needle. The movement of the clamp and the movement of the needle receptor may be proportional or indirectly proportional to the movement of the one or more tabs. Through mechanical linkages, such as those depicted in the various embodiments contained herein, the movement of the one or more tabs will effect a movement of a clamp puller, which in turn pulls a tension element attached to the clamp elements, thereby causing the clamp to open. The linear movement of the clamp puller is greater than the linear movement of the one or more tabs; while the linear movement of the needle receptor portion against the sealing material will be less than the linear movement of the one or more tabs. The linear movement of the needle receptor portion against the sealing material is preferably less than that of the tab movement, as a result of the creation of mechanical advantage, to apply a greater compressive force over a shorter travel, using techniques known to those skilled in the art. In this manner, the device is configured to apply a compressive force to the sealing material, creating mechanical advantage in order to apply a compressive force, as is known to those skilled in the art, where the force will be able to deform the sealing material in order to create the seal. For this embodiment of the device having mechanical linkages to effectuate clamp actuation and compression of the sealing material, it is contemplated that the linear movement of the tabs will be in the range of 1-5 millimeters, preferably in the range of 2-4 millimeters, and more preferably 2-3 millimeters. From this tab movement, it is anticipated that the linear action of the clamp puller to open the clamp will be at least 150%, at least 200%, or at least 300% of the movement of the tabs; while the movement of the needle receptor will be in the range of less than 50%, less than 30%, or less than 20% of the movement of the tabs.

In another embodiment, the safety mechanism comprises a subcutaneously located, palpable button, and similar to a "pen click" mechanism, where the palpable button may be manipulated to alternate between a first state and a second state. While in a first state, the palpable button prevents movement of the one or more tabs, thereby preventing the clamp sealing the lumen from opening; and while in a second state, the palpable button frees the one or more tabs for actuation, such that the clamp can be opened. Preferably, the palpable button, in a first state, serves to prevent substantially all movement of the subcutaneous tabs, until such a point as the button has been depressed. Once the palpable button is depressed, and is in the second state, the one or more tabs may then be pressed to cause the clamp to open and the palpable button, while in the second state is further arranged to maintain the one or more tabs in the actuated position, and thereby ensures the clamp remains in an open state, until such a point in time at which the palpable button is depressed again, and caused to revert to the first state, whereupon multiple actions occur: the one or more tabs are released, causing the clamp on the lumen to be closed by spring tension as the clamp puller returns to its original location; the funnel portion moves away from the sealing material, and halts the compression upon the sealing material, thereby releasing the seal grasping the needle in the funnel is released, whereupon the needle may be withdrawn.

In the use of this embodiment of the device, it is contemplated that the operator will direct a hollow needle to penetrate the skin, and subcutaneously enter the wide mouth end of the funnel shaped element of the needle receptor. As the needle is advanced deeper into the needle receptor, it advances through an opening in a sealing material positioned at or near a narrowed portion of the funnel of the needle receptor. As the needle is advanced through the opening in the sealing material, it displaces a sealing rod that is aligned coaxially with the axis of the needle receptor. The needle is arranged along an axis that extends through the center of the funnel and extends tangentially to a spherical chamber within the device. The spherical chamber is in fluid communication with a lumen extending distally towards the anastomosis junction. The needle is advanced along the axis until the distal tip of the needle is in fluid communication with the interior of the spherical chamber. In an embodiment, the needle is advanced to the location where the distal tip of the needle located tangential to or is aligned with a tangential opening into the interior of the spherical chamber. At this point, the palpable button of the safety mechanism may be depressed. With the palpable button depressed, in a manner similar to a "pen click", the safety mechanism will now allow the user to manipulate at least one tab, preferably two tabs, by applying a pressure and causing movement of the tab. The movement of the one or more tabs will cause the action of mechanical linkages, which result in the actuation of the clamp adjacent to the anastomosis junction to open, and also cause at least a portion of the funnel of the needle receptor to move in a distal direction, whereupon compressive force is applied the sealing material. The sealing material is thus squeezed between the housing of the device and the funnel, and in response, the sealing material constricts the opening through which the needle is directed, thereby sealing tightly around the outside surface of the needle, and thereby preventing fluid flow around the periphery of the needle. The movement of the one or more tabs is restrained by the safety mechanism, allowing the user to release the pressure of the tabs, and have the tabs retain their actuated position. In this manner, the clamp is maintained open, allowing fluid flow through the lumen, and maintaining the seal around the needle.

In use of the embodiment of the device having the tab actuated clamps, it is contemplated that two or more of these devices may be placed for dialysis. In this instance, it is anticipated that dialysis would occur where each device is implanted and anastomosed to a blood vessel, where first device is in fluid communication with the needle that serves to withdraw blood, typically from the arterial system, from the patient for the dialysis procedure, and the second device is in fluid communication with the needle that is returning dialyzed or filtered blood to the patient, typically into the venous system. Upon completion of the dialysis treatment, the fluid line for each device would be flushed with an amount of saline, or any other suitable flushing liquid to clear the line. After flushing, the palpable button of the safety mechanism may then be depressed, thereby returning the tabs to their original state and sealing the lumen by closing the clamp at the anastomosis junction, and further releasing seal of the sealing material around the periphery of the needle, such that the needle may then be withdrawn. As the needle is withdrawn from the needle receptor, the sealing rod, which had been displaced by the advancing needle, will return to its original position within the sealing material, thereby preventing fluid transfer in or out through the funnel of the needle receptor.

In the event that the needle is removed from the patient during dialysis, the sealing rod would be urged proximally into the opening in the sealing material left by the removal of the needle, thereby preventing the free flow of fluid through the device. This is especially important where the lumen is anastomosed to the arterial system, as the blood pressure is higher than in the venous system, and would if left unchecked, potentially cause significant blood loss to the patient. Thus the embodiment of the device featuring a sealing rod provides an automatic safety seal to prevent unchecked flow through the device in the event that the needle is removed while the clamp remains in an open position, and there is fluid communication between the needle receptor and the blood vessel.

In another embodiment, the subcutaneous vascular access device, comprises a needle receptor, a lumen (which may be referred to as a device lumen, in order to distinguish the element from a native bodily lumen), a lumen clamping means, and a clamp manipulator (In certain orientations, the clamp manipulator may be referred to as a component of the lumen clamping means, which is just for ease of illustration.). In these types of embodiments said needle receptor is arranged to accept a needle having a distal tip that is inserted from outside the body, and to provide positioning means for the placement of said needle.

In an embodiment, the lumen is arranged to contact said needle receptor at a first location and with said lumen being arranged to be anastomosed to a native body lumen at a second location. The lumen is further designed to have a cross section that remains nearly circular, but other shapes may be utilized so long as no geometric feature provides an eddy or other stagnate region, as this may lead to clotting or other cascades of difficulties. Similarly, irregularities in the vessel wall that cause turbulent or otherwise irregular flow will cause a different set of problems; all of which will decrease the efficiency of the device, render it unusable, or harm the patient in a worst case situation.

For the various embodiments described herein, the lumen clamping means generally comprises at least two clamping members. These members are optimally arranged to compress said lumen at a location between said first location and said second location, in an orientation substantially parallel to said lumen. It is believed that a parallel orientation is optimal, however, it is contemplated that lumen characteristics (including anastomosis design and characteristics) and fluid mechanics may dictate that a slight offset from parallel may provide a better seal with optimal flow characteristics. Therefore, a range of clamp orientations are contemplated in this disclosure. The goal of this element is primarily to provide a seal along said anastomosis and prohibit fluid flow therethrough, while maintaining an even flow of blood or other fluid through the native body lumen.

The shape of the clamping members may be generally circular in cross-section, to provide a linear region of highest clamping stress; however, lumen design and materials may dictate that a square or rectangular cross-section may provide an optimum sealing profile. Therefore, these and various contacting shapes are within the contemplation of this disclosure.

In another embodiment, a clamp manipulator, also referred to as a clamp manipulator or manipulation means, may be used. In an embodiment, the clamp manipulator may comprise elements that actuate mechanical linkages which directly drive the opening of clamp, and actuate a sealing mechanism around a needle, as has been previously discussed. For example, the action of the clamp manipulator may occur as one or more tabs are pressed by the user, the tabs through mechanical linkages convert the movement to a linear movement of a clamp puller, which is connected by a tension element to the clamping members, which react by opening and unsealing the lumen to allow fluid flow therethrough. In an embodiment, the clamp members are spring held by spring tension in a closed position, unless the clamp puller is retracted with a force to overcome the spring tension. Additionally, the one or more tabs when pressed, are urged against a spring, such that upon release, the spring tension pushes the tabs back to their original state, and reversing the movements caused by the action of the one or more tabs. In another embodiment, the clamp manipulator may comprise at least one tab rotatably attached to at least one axial support member, wherein the depressing of said tab causes rotation which may serve to engage a gear assembly which is arranged to pressurize a fluid to drive said fluid driven member.

In various embodiments described herein, the aforementioned clamp manipulator may further comprise at least a second tab. For the embodiment having hydraulic operation, the second tab may be rotatably attached to a second axial support member. For the embodiment relying on mechanical linkages to actuate the clamp, the second tab is preferably arranged to operate in concert with the first tab, such that the tabs may be squeezed towards each other, and the movement of each tabs are coupled together to reduce the force that each tab would have to exert alone to perform the tasks of opening the clamp, and tightly sealing around the needle, as has been described previously. Regardless, of whether a single or dual tab assembly is used, the tab or tabs are arranged to allow two fingers to provide adequate force to effect the required actions, such as clamp opening and sealing. It is contemplated that for a multiple tab assembly, each tab may be arranged to operate independently, or alternatively perform dissimilar actions. For example, a first tab may be configured to actuate the clamp, and the second tab may actuate the sealing around the needle. The clamp manipulator may further comprise locking means, wherein said locking means secures said tab(s) at a predetermined amount of travel. Additionally, a preferred embodiment locking means is arranged to unlock following the application of additional pressure to said tab(s) while they are in the secured state. This tab, or arrangement of tabs, are preferably palpable from outside the body.

These various embodiments containing needle receptors, further comprise a plurality of needle receptors, with said receptors being located longitudinally along said lumen such that said needle may be introduced at a plurality of locations.

In yet another embodiment of a subcutaneous vascular access device, there are basically four preferred elements a device lumen, a needle receptor, lumen clamping means, and a clamp manipulator. In this embodiment the device lumen has a distal end and a proximal end defining a lumen length. The device lumen may also have an anastomosis at said distal end, wherein said anastomosis serves to connect said device lumen to a native body lumen.

A needle receptor may be arranged to be palpable from outside the body and anchored along the lumen length to provide fluid communication therewith.

The entry needle may be assisted or guided, in this embodiment, by a funnel shaped entry port arranged to accept and guide said needle toward said rotating member. Further, the funnel shaped entry port may be palpable, so that the needle stick in the skin may be more exact.

A preferred embodiment will also contain a lumen clamping means arranged at the proximal end of said device lumen. This lumen clamping means may include a manipulation means comprising two tabs each palpable under the skin.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments may omit steps shown and described in connection with the illustrative methods. Some embodiments may include steps that are not shown and described in connection with the illustrative methods.

Illustrative embodiments of apparatus and methods in accordance with the principles of the invention will now be described with reference to the accompanying drawings, which form a part hereof. The drawings show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

The apparatus and methods of the invention will be described in connection with exemplary embodiments. It is to be understood that other embodiments may be utilized and structural, functional and procedural modifications may be made without departing from the scope and spirit of the present invention.

FIG. 1 shows an illustration of the needle receptor 101 having a funnel opening 105, the clamp manipulator 100, and the portion of the clamp manipulator referred to in certain embodiments as the one or more tabs 110, the palpable button 115. This figure also shows the needle 121, in place for insertion into the funnel opening 105. Also depicted are tension element 01 14141 connected to clamp arms 150 configured to clamp the lumen 160 at a point adjacent to the anastomosis with the blood vessel.

Figure 2:
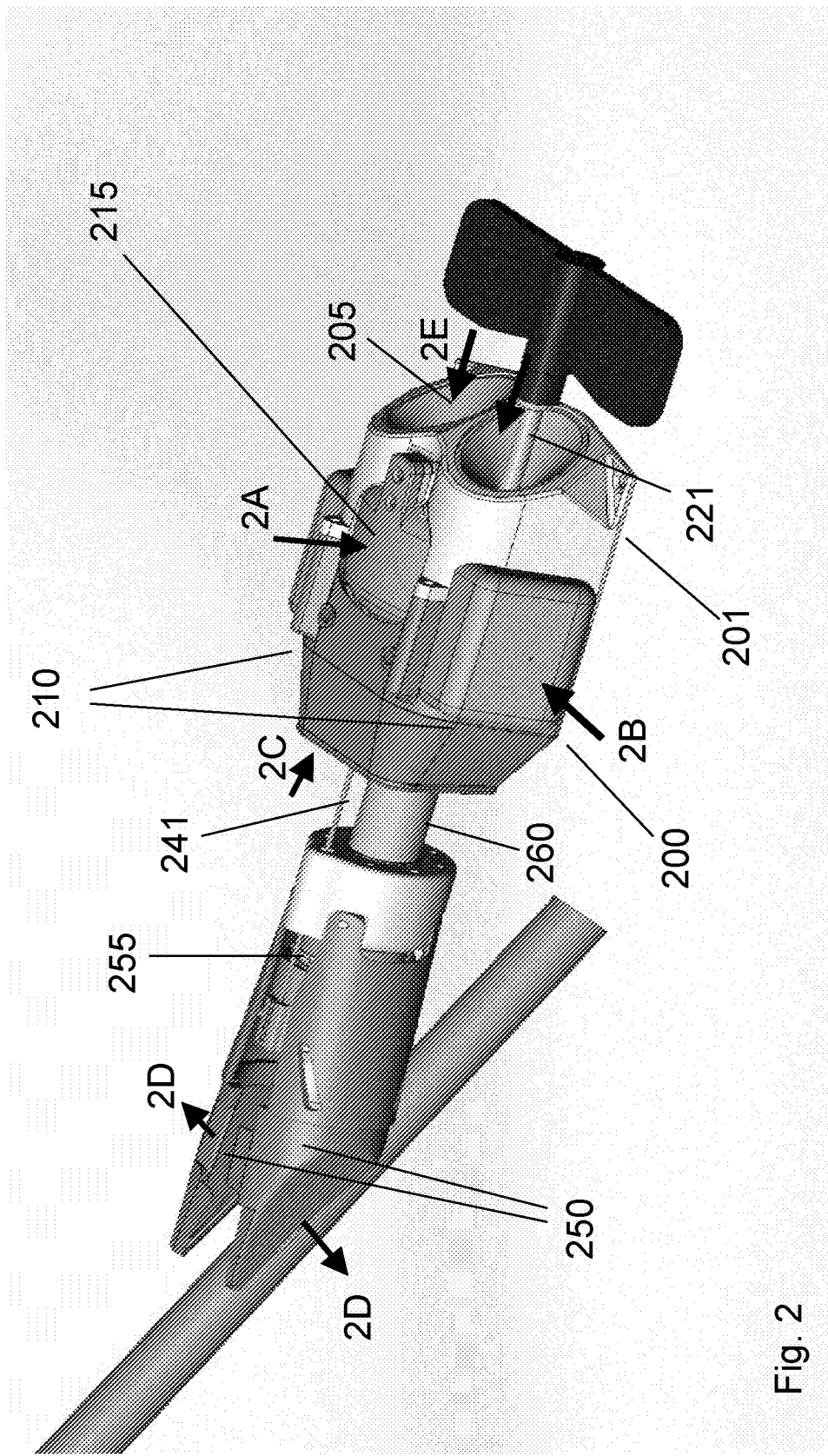
FIG. 2 shows illustrative apparatus in accordance with principles of the invention.

FIG. 2 depicts the needle 221 having been advanced into the needle receptor 201 through the funnel portion 205. With the needle inserted into the needle receptor 201, the palpable button 215 may be depressed in the direction indicated by arrow 2A, so that the palpable button is moved from a first state to a second state. When the button 215 is in a first state, it is configured to mechanically prevent movement of one or more tabs 210. However, once button 215 is in a second state, the one or more tabs 210 may then be actuated by pressing in the tab, as represented by arrow 2B. In embodiments having two tabs on opposing sides of the clamp manipulator 200, corresponding forces may be applied to squeeze both tabs 210 at the same time, to actuate the mechanical linkages within the clamp manipulator 200. Actuation of the clamp manipulator 200 will cause tension element 241 to be pulled in a proximal direction as depicted by arrow 2C, whereupon the clamp arms 250 are opened, as depicted by arrows 2E to allow fluid flow through the lumen 260. As the clamp arms 250 are urged open, a clamp spring 255 is energized, such that clamp spring would urge the clamp arms to a closed position, but for the tension applied via tension element 241. The clamp actuator 200 additionally is mechanically linked to the funnel portion 205 of needle receptor 201, such that as the one or more tabs 210 are pressed, the funnel portion is urged in a distal direction, as shown by the force arrows 2E.

Figure 3:
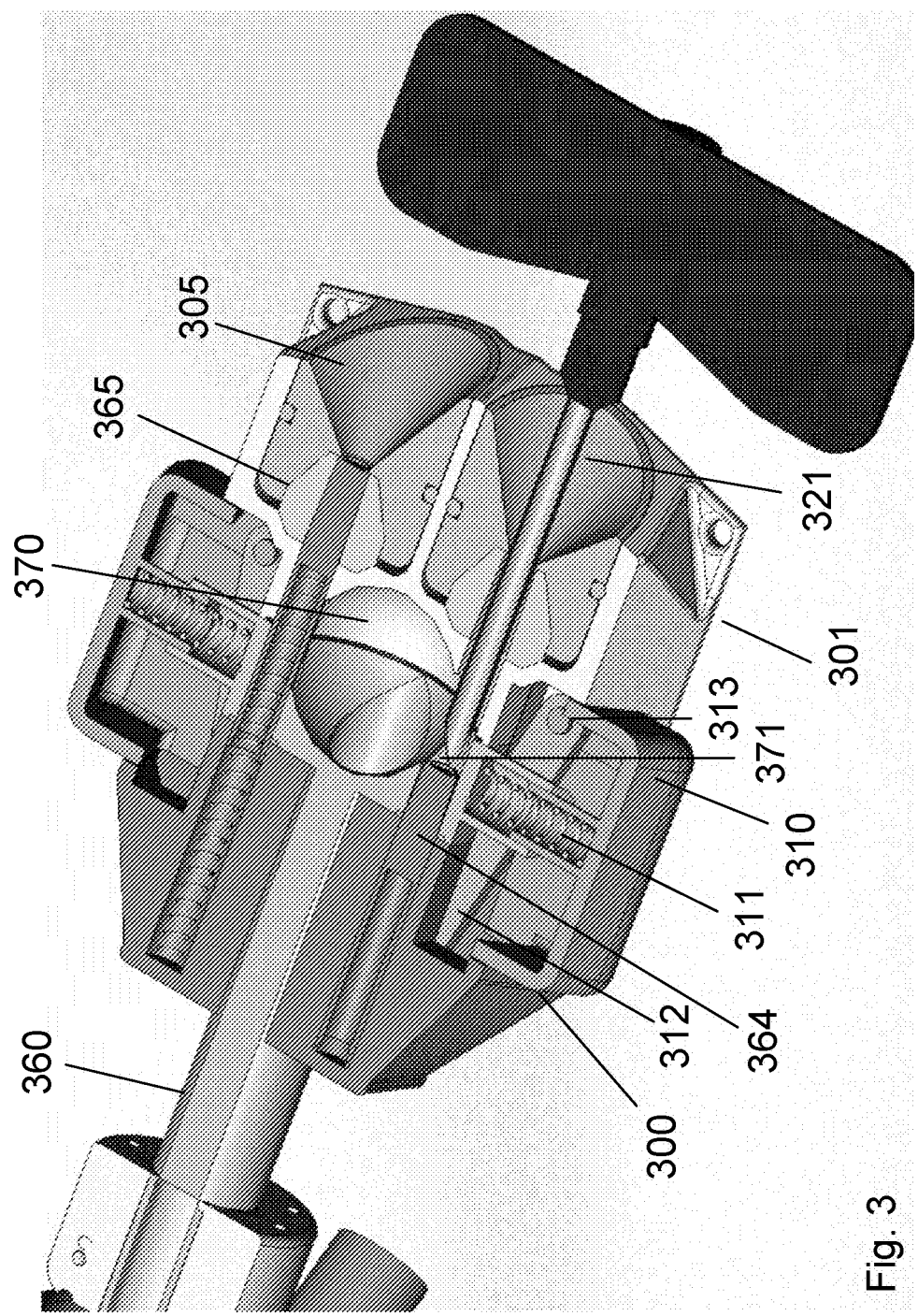
FIG. 3 shows illustrative apparatus in accordance with principles of the invention.

FIG. 3 depicts a cross-section view of the internal elements of the needle receptor 301, and the clamp manipulator 300. The needle 321 is depicted as having been advanced through the mouth of the funnel 305, and through the elastic sealing material 365, and displacing a spring mounted sealing rod 364. The needle receptor 301 provides, in this embodiment, 2 paths for alternating needle penetration when the blood system is being accessed, so as to afford healing of the skin subsequent to needle penetration, prior to the subsequent access. The needle 321 enters along an axis the intersects tangentially with a spherical chamber 370, which is in fluid communication with the lumen 360. It is contemplated that the spherical chamber 370 may alternatively be a non-spherical shape, for example ovoid, but in any embodiment, it is preferred that sharp corners are avoided, so as to avoid eddies or poorly flowing regions in the chamber that would otherwise promote clotting or biological build up in the poorly flowing region. It is recognized that a spherical chamber, having tangentially located ports 371, promotes even flow through the entirety of the chamber, during the period of time when blood is flowing through the device, and additionally upon being flushed with saline, will effectively flush the blood material from the device, such that the closed volume, when not being accessed remains filled with the saline flush. FIG. 3 further depicts the one or more tabs 310, which upon being released for movement by the pressing of the palpable button (not shown), each of the tabs 310, being palpable through the skin, may be urged by the operator to move, and overcome the resistance of tab spring, The movement of the tab 310, in turn, acts upon mechanical linkages a portion of which is shown in FIG. 3, where first rigid link 312, connected to the tab via first pivot 313. The mechanical output from pressing upon tabs 310 is depicted in FIG. 4.

Figure 4:
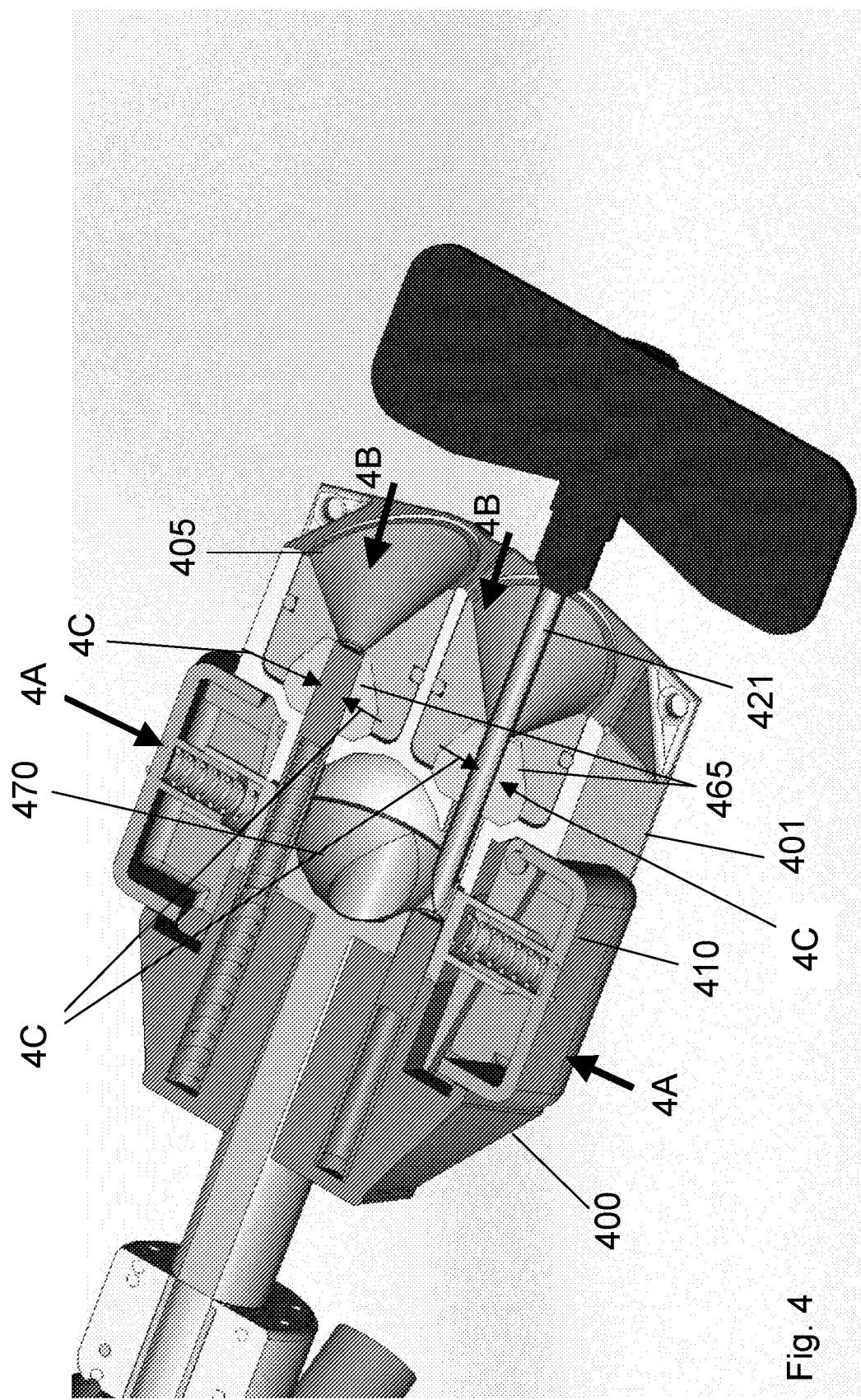
FIG. 4 shows illustrative apparatus in accordance with principles of the invention.

FIG. 4 depicts the needle receptor 401 and clamp manipulator 400. In FIG. 4, the one or more tabs 410 are depicted as having been pressed and moved inwards towards the spherical chamber 470, in the direction depicted by arrow 4A. The movement of the one or more tabs 410, in turn acts upon a series of mechanical linkages to cause the funnel 405 of the needle receptor to move in the direction depicted by arrows 4B, and applying compressive force to elastic sealing material 465, which due to being constrained from movement by the construction of the clamp manipulator 400, responds by compressing axially, as depicted by the arrows 4C, thereby forming a seal around the needle 421. The movement of the one or more tabs 410 is similarly conveyed by mechanical linkages to cause the clamp to open, as will be discussed.

Figure 5:
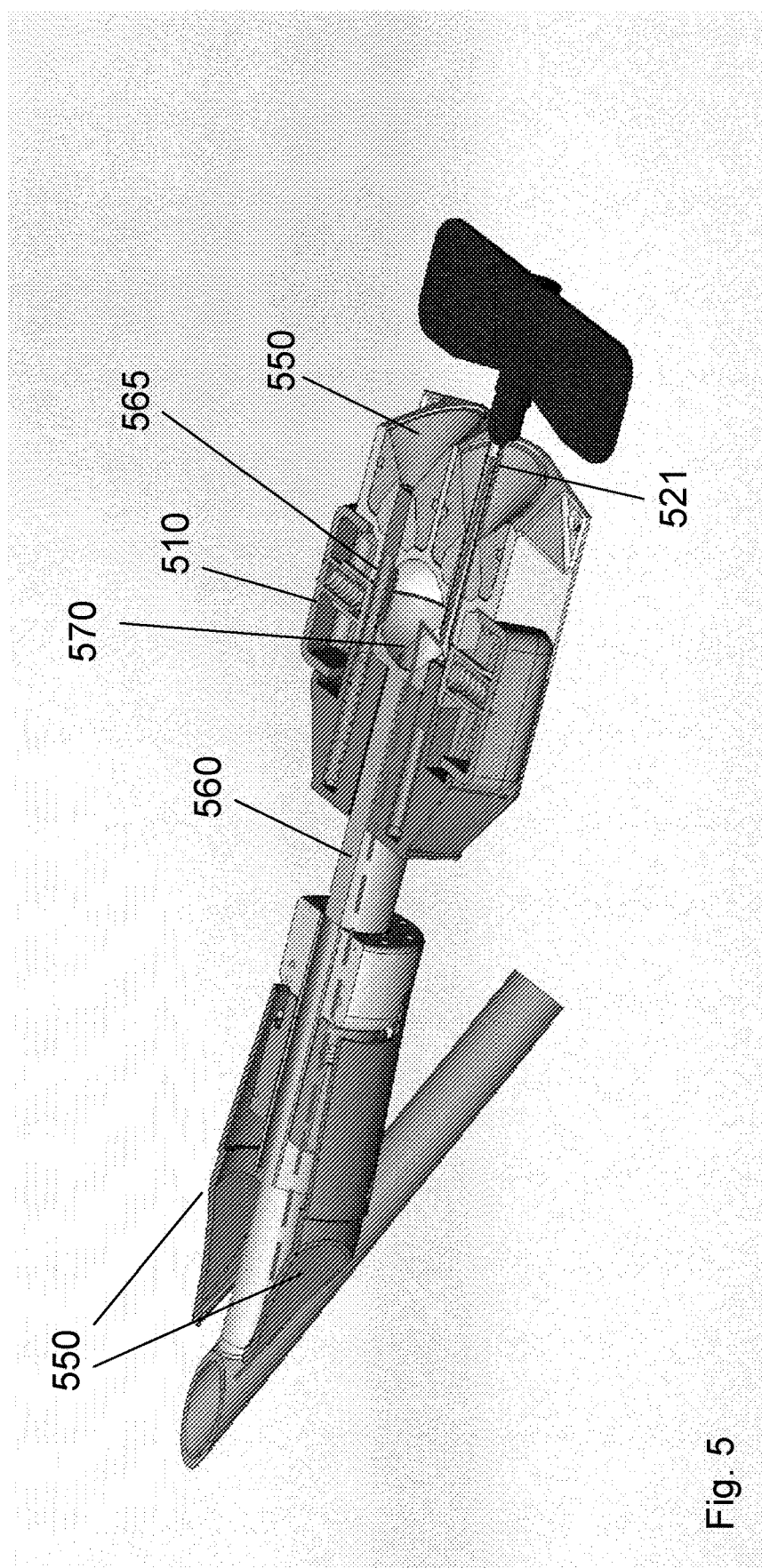
FIG. 5 shows illustrative apparatus in accordance with principles of the invention.

FIG. 5 depicts one embodiment of the subcutaneously implanted device while in a state allowing blood flow therethrough. In this embodiment, the one or more tabs 510 are urged inwards, as previously discussed, and the funnel 505 has been urged against sealing material 565 to seal tightly around needle 521. Additionally, clamp arms 550 have been caused to open, such that there is now fluid communication between the native body blood vessel, the lumen 560, the spherical chamber 570, and the interior of the needle 521. In this manner, blood is able to flow through the fluid pathway, to allow a medical procedure, such as dialysis to occur. By using two devices in tandem, it is anticipated that blood could be withdrawn from an anastomosis with the arterial system, or a graft, flow through the subcutaneously implanted device, and be delivered to a dialysis machine outside of the body. After the blood is filtered or treated, the blood may be returned through a second device anastomosed to a venous system, or graft, such that the blood flows through the needle, then through the lumen, and to the venous system. It is contemplated that in a less preferred use, the direction of flow through the device may be reversed after a period of time, where an amount of blood is removed from the patient, treated, and returned through the same device back into the blood system of the patient.

Figure 6:
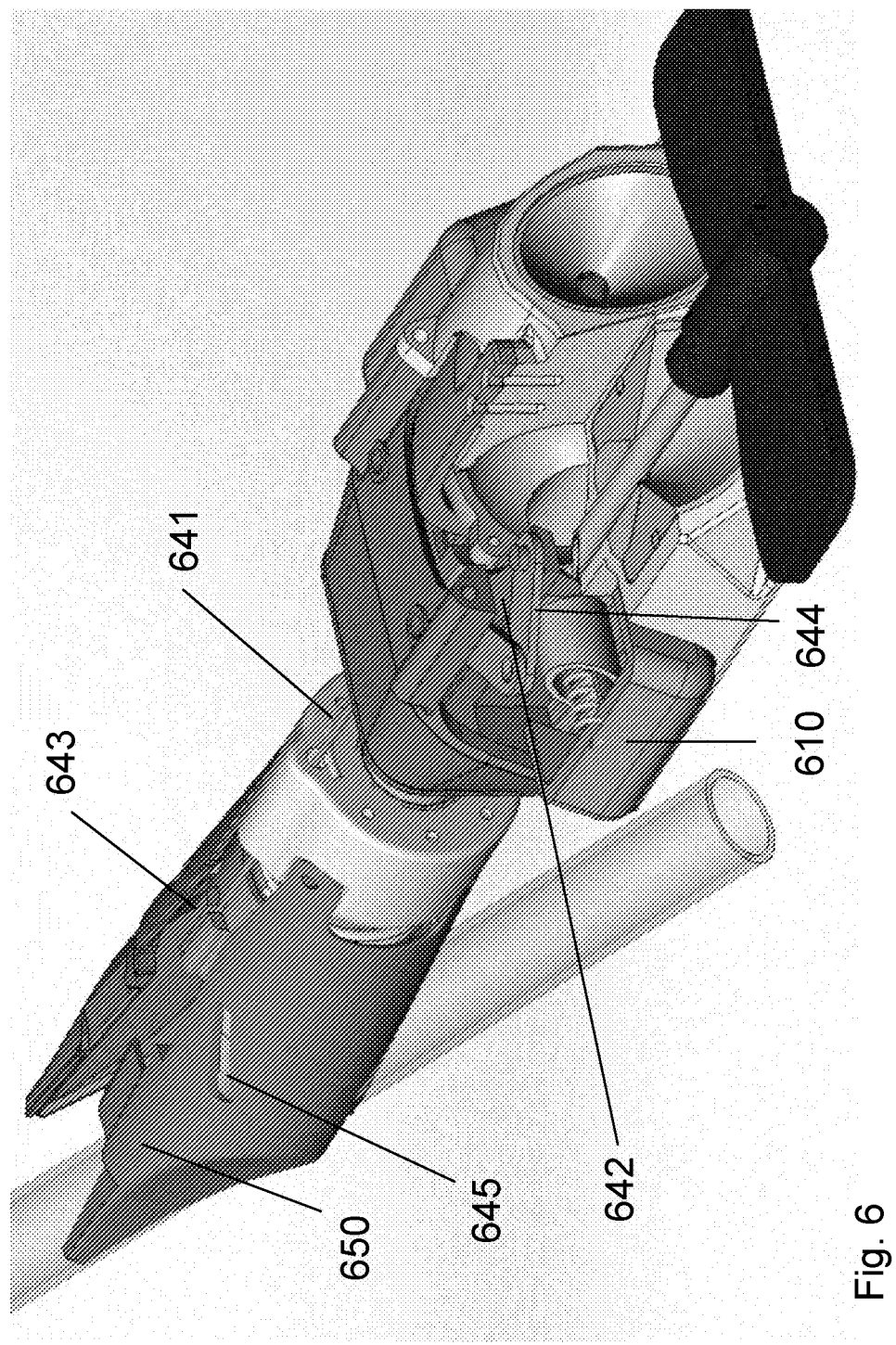
FIG. 6 shows illustrative apparatus in accordance with principles of the invention.

FIG. 6 is different view of the device in the same condition depicted in FIG. 5, and depicts the clamp arms 650 having been opened by the action the one or more tabs 610, acting via mechanical linkages comprising at least a second rigid link 644, which is secured to the body of the tab at one end, and to a cable puller 642 at the other end. The second rigid link 644 serves to transfer the movement of the tab 610 into a proximally directed (in a direction away from the anastomosis) movement of puller 642. The proximally directed movement of the puller in turn pulls on the tension element 641, which may be a cable or tension rod. The tension element 641 is secured at its distal terminus to a fixation element 643, and acts in cooperation with the clamp arms, to open the clamp arms as the fixation element is moved proximally. This may be accomplished, for example, by pins or protruding elements (as can be seen with reference to FIG. 1) affixed to the fixation element 643, that ride in cam slots 645 in the clamp arms 650, such that the pins riding in the angled cam slots 645 force the clamp arms to open, when the puller 642 is moved proximally, It is understood that a variety of mechanical linkage arrangement may alternatively be utilized to clause the clamp to open, and in light of this teaching, those of ordinary skill in the art can generate additional embodiments and modifications without departing from the spirit of or exceeding the scope of the principles of the invention.

Figure 7:
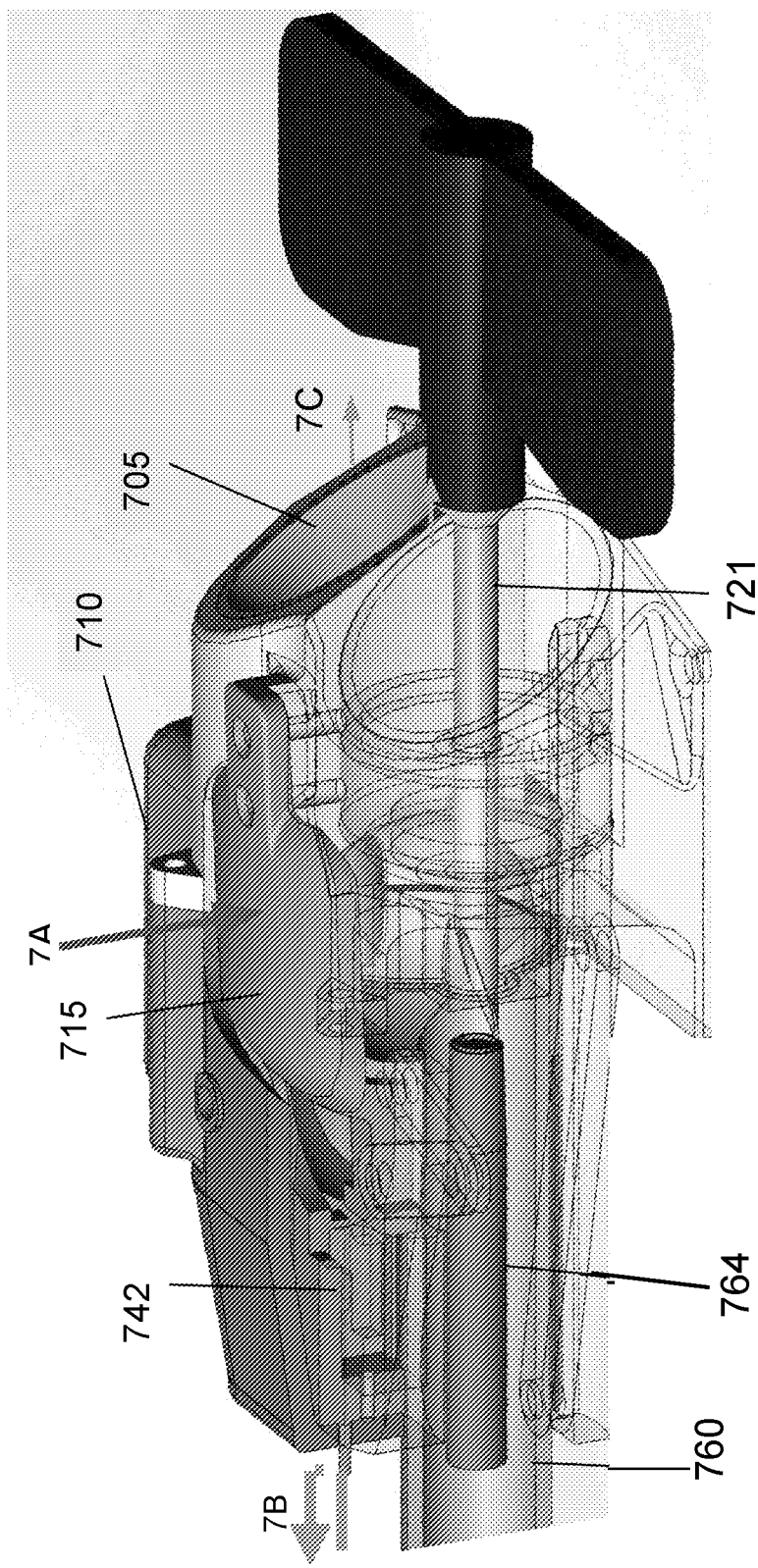
FIG. 7 shows illustrative apparatus in accordance with principles of the invention.

FIG. 7 depicts the device actions to be performed after the medical procedure, typically blood dialysis, has been completed, and the fluid pathway has been preferably flushed with saline, or any other suitable fluid to clear the pathway. In order to seal off the lumen 760, the user depresses the palpable button 715 in the direction shown by arrow 7A, causing the button to revert from the second state to the first state. While the button remained in the second state, the inward movement of the one or more tabs 710 was restrained; and as the button enters the first state, the tabs are urged back to their original position by the springs (see tab springs 311 of FIG. 3). The movement of the tabs to their original position reverses the movement of the mechanical linkages described previously, such that the clamp arms are caused to clamp and seal the lumen 760, as the tension upon the tension element is released (represented by the arrow 7B, and the puller 742 returns to its original position. Additionally, the tab movement allows the ring seal formed by the elastomeric material around the needle 721 to release, as the funnel portion 705 is moved proximally in the direction shown by arrow 7C. As needle 721 is withdrawn, the spring loaded sealing rod 764 is urged against the retreating needle, until such a point as the sealing rod is through the sealing material, thereby completing a seal in the proximal end of the fluid pathway while the device remains in an idle position. Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments of the invention may omit steps shown and described in connection with the illustrative methods. Some embodiments of the invention may include steps that are not shown and described in connection with the illustrative methods.

The invention may be operational with numerous other general purpose or special purpose computing system environments or configurations. For example, control of expandable, contractible and otherwise moveable apparatus may be controlled by a computer system. Examples of well-known computing systems, environments, and/or configurations that may be suitable for use with the invention include, but are not limited to, personal computers, server computers, hand-held or laptop devices, mobile phones and/or other personal digital assistants ("PDAs"), multiprocessor systems, microprocessor-based systems, set top boxes, programmable consumer electronics, network PCs, minicomputers, mainframe computers, distributed computing environments that include any of the above systems or devices, and the like. In a distributed computing environment, devices that perform the same or similar function may be viewed as being part of a "module" even if the devices are separate (whether local or remote) from each other.

The invention may be described in the general context of computer-executable instructions, such as program modules, being executed by a computer. Generally, program modules may include routines, programs, objects, components, data structures, etc., that perform particular tasks or store or process data structures, objects and other data types. The invention may also be practiced in distributed computing environments where tasks are performed by separate (local or remote) processing devices that are linked through a communications network. In a distributed computing environment, program modules may be located in both local and remote computer storage media including memory storage devices.

Although the invention has been described in terms of particular embodiments and applications, one of ordinary skill in the art, in light of this teaching, can generate additional embodiments and modifications without departing from the spirit of or exceeding the scope of the principles of the invention. Accordingly, it is to be understood that the drawings and descriptions herein are proffered by way of example to facilitate comprehension of the invention and should not be construed to limit the scope thereof. Persons skilled in the art will appreciate that the present invention can be practiced by other than the described embodiments, which are presented for purposes of illustration rather than of limitation.

Thus, systems and methods for hydraulically controlled arterial/venous access, as well as mechanical linkage enabled arterial/venous access, have been provided. Persons skilled in the art will appreciate that the present invention can be practiced by other than the described embodiments, which are presented for purposes of illustration rather than of limitation. The present invention is limited only by the claims that follow.

What is claimed is:

1. A subcutaneous vascular access device designed for repeated access to a native body vessel comprising:
    a lumen and a housing, said lumen extending between said housing located at a lumen proximal end and a lumen distal end configured to be attached to an anastomosis junction with a blood vessel, said anastomosis junction being located at the lumen distal end, wherein said lumen is configured to be in fluid communication with the native body vessel and said housing,
    wherein fluid flow through said lumen is selectively sealed by a clamp,
    wherein said housing comprises at least one funnel shaped needle receptor, a hollow spherical chamber, and at least one clamp actuator that is mechanically linked to said clamp and is arranged to selectively actuate said clamp,
    wherein said at least one funnel shaped needle receptor is selectively in fluid communication with said hollow spherical chamber and said at least one funnel shaped needle receptor is arranged coaxially on an axis that intersects said hollow spherical chamber at a point that is tangential to said hollow spherical chamber, and further, wherein said lumen is in fluid communication with said hollow spherical chamber.

2. The subcutaneous vascular access device of claim 1, wherein said at least one clamp actuator comprises at least one tab that is palpable from outside the body, is arranged to be manually actuated by a user, such that upon actuation, an actuating force applied to said at least one tab is transmitted through a mechanical linkage to said clamp, thereby causing said clamp to open and allow fluid flow through said lumen.

3. The subcutaneous vascular access device of claim 2, wherein said at least one funnel shaped needle receptor further comprises an elastomeric sealing material having an opening therein arranged to permit passage of a hollow needle therethrough.

4. The subcutaneous vascular access device of claim 3, wherein said actuating force is further transmitted through the mechanical linkage to said at least one funnel shaped needle receptor, and applies pressure to said elastomeric sealing material which is arranged to deform and tightly conform around an outer surface of said hollow needle, thereby forming an impenetrable seal with said outer surface of said needle.

5. The subcutaneous vascular access device of claim 3, wherein said hollow needle, upon insertion through said opening in said elastomeric sealing material causes the displacement of a sealing rod slidably arranged in said opening, whereupon said displacement causes energy to be stored, such that upon removal of said hollow needle, said sealing rod is arranged to utilize said energy to reverse travel through said opening, thereby sealing said opening.

6. The subcutaneous vascular access device of claim 5, wherein the stored energy serves to provide a fail-safe mechanism to automatically seal said opening in said elastomeric sealing material upon intentional or accidental removal of said hollow needle.

7. The subcutaneous vascular access device of claim 2, wherein said at least one clamp actuator further comprises a lock-out button arranged to be operable in a first position and a second position, wherein said lock-out button is palpable from outside the body, wherein said lock-out button, while in the first position, prevents opening of said clamp, and when said lock-out button is in the second position, allows the opening of said clamp.

8. The subcutaneous vascular access device of claim 2, wherein said at least one clamp actuator is linked to said clamp by a pull cable, a push rod, or a lever arrangement, such that movement of said at least one tab results in a proportional movement of said clamp.

9. The subcutaneous vascular access device of claim 8, further wherein the movement of said at least one tab results in a proportional movement of said at least one funnel shaped needle receptor, wherein the movement of said at least one funnel shaped needle receptor is less than 50% of the movement of said clamp.

10. A subcutaneous vascular access device designed to selectively provide fluid communication between a needle inserted from outside the body and a native bodily vessel within a body comprising:
- a lumen and a housing, said lumen extending between said housing located at a lumen proximal end and a lumen distal end configured to be attached to an anastomosis junction with a blood vessel, said anastomosis junction being located at the lumen distal end, wherein said lumen is configured to be in fluid communication with the native bodily vessel and said housing, wherein fluid flow through said lumen is selectively sealed by a clamp, with said clamp being arrangable adjacent and proximally locatable relative to said anastomosis junction, with said anastomosis junction being further arrangable to accept an anastomosis for affixing said lumen to the native bodily vessel;
- wherein said housing comprises at least one funnel shaped needle receptor, a hollow spherical chamber, a safety button, and at least one clamp actuator that is mechanically linked to said clamp through a lever system whereby said at least one clamp actuator is arranged to selectively actuate said clamp;
- wherein said at least one funnel shaped needle receptor is selectively in fluid communication with said hollow spherical chamber and said at least one funnel shaped needle receptor is arranged coaxially with an axis that intersects said hollow spherical chamber at a point that is tangential to said hollow spherical chamber, and further, wherein said lumen is in fluid communication with said hollow spherical chamber; and
- wherein said at least one clamp actuator further comprises at least one tab, wherein said at least one tab is connected to said lever system in a rotationally sliding arrangement.

11. The subcutaneous vascular access device of claim 10, wherein said at least one funnel shaped needle receptor further comprises an elastomeric sealing material having an opening therein arranged to permit insertion of said needle therethrough, whereupon said needle is in fluid communication with said lumen through a contiguous pathway that includes flow through said hollow spherical chamber.

12. The subcutaneous vascular access device of claim 11, wherein said safety button is arranged to be operable in positions comprising a locked state and an unlocked state, wherein said locked state prevents movement of said at least one tab, and pressing said safety button toggles it to said unlocked state where said at least one tab may be depressed.

13. The subcutaneous vascular access device of claim 12, wherein depressing said at least one tab causes said lever system to displace said at least one funnel shaped needle receptor and a cable member; with said at least one funnel shaped needle receptor arranged to compress said elastomeric sealing material between said at least one funnel shaped needle receptor and said housing in response to said displacement; and
wherein said cable member is slidably arranged between said at least one clamp actuator and said clamp, wherein said displacement causes said cable member to translate force from said at least one clamp actuator to said clamp, where said force serves to cause said clamp to be manipulated from a closed position to an open position, with said open position being arranged to allow fluid communication between said lumen and said native bodily vessel.

14. The subcutaneous vascular access device of claim 13, wherein said housing further comprises a springback mechanism arranged to absorb springback energy during the displacement of said cable member, with said springback mechanism arranged to release said springback energy upon the pressing of the safety button when said safety button is in the unlocked state.

15. The subcutaneous vascular access device of claim 14, wherein the release of said springback energy forces said at least one tab back to its original position, thereby releasing the force on said cable member such that said cable member returns to its original position.

16. The subcutaneous vascular access device of claim 15, wherein said cable member causes said clamp to close, thereby clamping said lumen and discontinuing said fluid communication between said lumen and said native bodily vessel.

17. The subcutaneous vascular access device of claim 15, wherein release of said springback energy further serves to move said at least one funnel shaped needle receptor back to its original position.

18. The subcutaneous vascular access device of claim 17, wherein the return of said at least one tab to its original position together with the return of said at least one funnel shaped needle receptor to its original position seals said lumen proximal end and said lumen distal end, thereby creating a volume of fluid stored in said device during non-use.

19. The subcutaneous vascular access device of claim 11, wherein said housing further comprises:
- a second funnel shaped needle receptor of said at least one funnel shaped needle receptor, arranged coaxially with an axis that intersects said hollow spherical chamber at a point that is tangential to said hollow spherical chamber, and
- at least a second tab, wherein said second tab forms a part of said at least one clamp actuator, with said second tab further arranged to be connected to said lever system in a rotationally sliding arrangement.

* * * * *